(12) United States Patent
Kendall et al.

(10) Patent No.: US 6,620,441 B1
(45) Date of Patent: Sep. 16, 2003

(54) STABILIZED ACTIVE BROMINE BIOCIDAL SOLUTIONS

(75) Inventors: John K. Kendall, Magnolia, AR (US); Alireza M. Dadgar, Magnolia, AR (US); Bonnie G. McKinnie, Magnolia, AR (US)

(73) Assignee: Albemarle Corporation, Richmond, VA (US)

( * ) Notice: Subject to any disclaimer, the term of this patent is extended or adjusted under 35 U.S.C. 154(b) by 16 days.

(21) Appl. No.: 09/894,598

(22) Filed: Jun. 28, 2001

(51) Int. Cl.7 ............................ A01N 59/00; A61L 2/16; C02F 1/76
(52) U.S. Cl. ...................... 424/723; 424/613; 424/616; 424/661; 514/970; 514/973; 422/27; 210/754
(58) Field of Search .................................. 424/661, 723, 424/613, 616; 514/970, 973; 210/754; 422/27

(56) References Cited

U.S. PATENT DOCUMENTS

| | | | |
|---|---|---|---|
| 5,683,654 A | 11/1997 | Dallmier et al. | 422/14 |
| 5,795,487 A | 8/1998 | Dallmier et al. | 210/754 |
| 5,942,126 A | 8/1999 | Dallmier et al. | 210/756 |
| 6,007,726 A | 12/1999 | Yang et al. | 210/752 |
| 6,156,229 A | 12/2000 | Yang et al. | 252/186.1 |

OTHER PUBLICATIONS

Chemical abstracts 109:22420 (1988).*
Material Safety Data Sheet for Sodium Bromide, Albermarle PPC, Apr. 1993.*

* cited by examiner

*Primary Examiner*—John Pak
(74) *Attorney, Agent, or Firm*—Edgar E. Spielman, Jr.

(57) ABSTRACT

In producing aqueous microbiocidal solutions by oxidation of a water-soluble alkali metal bromide, an intolerable loss of active halogen species has been found to occur during a 10-day period immediately after the product solution has been formed. Surprisingly, this loss has been found to result from an alcohol impurity in the alkali metal bromide used in the process. By eliminating or at least sharply reducing the amount of alcohol impurity in the reaction mixture, products are formed which do not undergo the intolerable loss of active halogen content during the 10-day period.

17 Claims, No Drawings

STABILIZED ACTIVE BROMINE BIOCIDAL SOLUTIONS

BACKGROUND

Background relating to, and one common way of producing, stabilized active bromine biocidal solutions are illustrated in U.S. Pat. Nos. 5,683,654; 5,795,487; and 5,942,126 to Dalimier et al, the entire disclosures of which are incorporated herein by reference. The method involves mixing an aqueous solution of alkali or alkaline earth metal hypochlorite with a water-soluble bromide ion source such as sodium bromide, allowing these materials to react to form an aqueous solution of unstabilized alkali or alkaline earth metal hypobromite, adding an alkali metal sulfamate either as a solid or as an aqueous solution to the hypobromite solution, and recovering a stabilized aqueous alkali or alkaline earth metal hypobromite solution.

While this method does improve the stability of the aqueous alkali or alkaline earth metal hypobromite solutions formed by use of the alkali metal sulfamate, it has been discovered that the "stabilized" hypobromite solution loses some of its active halogen content and consequent biocidal capabilities over the course of about 10 days after the concentrated product solution has been made. Also some loss of the alkali metal base typically present in the final finished product solution has been found to occur during this same period of time.

THE INVENTION

After considerable effort, during which many possible reasons for these problems were investigated, the cause of the above problems has finally been discovered and overcome. Surprisingly, the problem has been found to originate with the water-soluble bromide ion source used in the process, and more particularly with an impurity present therein, an impurity which, even if its presence had been taken into consideration, would not have been expected to survive the processing used in forming the "stabilized" hypobromite solution.

Pursuant to this invention it has been discovered that the loss of active halogen content and consequent biocidal capabilities over the course of several days after the concentrated product solution has been made is due to the presence of small amounts of alcohol, typically methanol, present as an impurity in the water-soluble bromide ion source used in the process. In commercial practice sodium bromide used in the manufacture of these "stabilized" hypobromite solutions has contained relatively small quantities of methanol. However, not until this invention have the existence of, cause of, or any solution to, the present problems been known or appreciated.

Accordingly, pursuant to one embodiment of this invention an aqueous solution of a water-soluble bromide ion source such as sodium bromide is oxidized in an aqueous medium in the absence of a detrimental amount of alcohol impurity to active bromine species. In other words, the water-soluble bromide ion source used is free of a detrimental amount of any alcohol, and the overall oxidation process is conducted in the absence of a detrimental amount of any alcohol. By "detrimental amount" of an alcohol with reference to the bromide ion source is meant that the water-soluble bromide ion source is either completely free of any detectible quantity of an alcohol or if any alcohol impurity is present therein, the amount of such alcohol is so small that it exerts no intolerable adverse effect upon the activity of final active halogen solution (expressed as wt % of chlorine, and as determinable by starch-iodine titration) during a 10-day period immediately following preparation of the product solution if stored at room temperature no higher than 30° C. in the absence of light. Likewise "detrimental amount" of an alcohol with reference to the aqueous reaction solution and the final product solution formed in the process means that at all times during the process and during foregoing the 10-day period of storage under the conditions just specified, the solutions are either completely free of any detectible quantity of an alcohol or if any alcohol impurity is present therein, the amount of such alcohol is so small that it exerts no intolerable adverse effect upon the activity of the final active halogen solution (expressed as wt % of chlorine, and as determinable by starch-iodine titration) during the 10-day period immediately following preparation of the product solution if stored at room temperature no higher than 30° C. in the absence of light.

As is customary in the art of water treatment chemicals for control of microbiocidal activity, analytical results are conventionally expressed in terms of chlorine, even when the analysis actually involves bromine species or a mixture of both chlorine and bromine species. Generally speaking, if the amount of alcohol present in the bromide ion source is at such a level that the alcohol would be in excess of about 0.11 wt % of the final stabilized active halogen solution, such amount of alcohol is a detrimental amount of alcohol as the loss of active halogen is intolerable and unacceptable. Amounts of alcohol of about 0.11 wt % and below are not deemed detrimental. If the amount of alcohol present in the bromide ion source is at such a level that the alcohol would constitute about 0.06 wt % or less of the final stabilized active halogen solution, the results are even better, and thus a maximum concentration of 0.06 wt % of alcohol, if any, based on the final product solution is preferred, and the lower the content of alcohol below this maximum, the better. Most preferred is the total absence of any detectable quantity of alcohol in the product solution.

Another embodiment of this invention is an aqueous microbiocidal solution having a pH of at least about 13 containing at least 4 wt %, and preferably at least 6 wt %, of stabilized active halogen species formed by oxidation of an alkali metal bromide, preferably sodium bromide, and incorporation of a stabilizer for the active bromine, preferably a source of sulfamate anion, such solution being characterized in that during the 10-day period immediately following its preparation, such product solution, if stored at room temperature no higher than 30° C. in the absence of light, undergoes no appreciable loss of active halogen content expressed in terms of wt % of active chlorine, and as determinable by starch-iodine titration.

The oxidation can be conducted in the absence of a stabilizer such as a sulfamate source, followed by mixing the stabilizer with the reaction solution containing the active halogen species to form a stabilized concentrated solution of active halogen. Alternatively, a small amount of the stabilizer can be present in the initial reaction solution and additional amounts of the stabilizer can be added during and after the oxidation. Irrespective of the pH of the reaction solution during the reaction, the pH of the final concentrated solution should be at least about 12 and preferably at least about 13, and thus if necessary, and preferably, a water-soluble inorganic base such as alkali metal hydroxide (most preferably sodium hydroxide) is added to the solution. As noted above, all stages of the process are conducted in the absence of a detrimental quantity of any alcohol such as methanol. Preferably the temperature is maintained below about 25° C. and more preferably below about 20° C. during the entire reaction.

In a preferred embodiment, this invention provides a process which comprises:

a) mixing an aqueous solution of alkali or alkaline earth metal hypochlorite with a water-soluble source of alkali metal bromide ion in the presence of a small amount of a water-soluble source of sulfamate ion;

b) allowing the solution formed in a) to undergo reaction to form a solution containing a mixture of stabilized and unstabilized active halogen species while mixing additional amounts of a water-soluble source of sulfamate ion to the reaction mixture; and c) mixing a water-soluble source of alkali metal base, preferably a 20 to 50 wt % aqueous solution of NaOH, to solution formed in b) to form a stabilized solution of active halogen species having a pH of at least about 12, and preferably at least about 13;

the process being further characterized in that each of steps a), b), and c) is performed in the absence of a detrimental quantity of any alcohol, such as methanol. The stabilized solution formed in c) preferably contains at least about 4 wt % of active halogen and more preferably at least about 6 wt % of active halogen, expressed as chlorine, as determinable by starch-iodine titration.

By conducting the above reaction in the absence of the detrimental quantities of alcohol, the final product solution of stabilized active halogen species does not undergo the extent of the loss of active halogen species that occurs when methanol or other alcohol is present, and that has occurred when methanol has been present.

Use can be made of any suitable known procedure for detection and/or determination of alcohol content of the water-soluble bromide ion source to be employed in the process. A recommended procedure for carrying out the alcohol content determination of an aqueous solution of the bromide ion source or an aqueous reaction mixture containing such bromide ion source involves use of gas chromatography. Thus, for example, a one gram sample of the aqueous solution or mixture is added to a 100 mL volumetric flask and is diluted to volume with distilled water. One microliter of this diluted solution is then analyzed by gas chromatography using the conditions that follow. The column used is a Porapak® QS column (a 6-foot column packed with silanized porous polymer beads, which have been treated with divinylbenzene and ethylvinylbenzene, and then silanized) available from Restek Corporation, 110 Benner Circle, Bellefonte, Pa. 16823), or an equivalent packed gas chromatograph column. The injector port is at 250° C., the detector is kept at 300° C., and the oven is held at 140° C. for the initial 3 minutes, after which the temperature is raised at a rate of 20° C. per minute, until the temperature reaches 230° C. The gas chromatograph is calibrated with an external standard containing ppm levels of the alcohol believed to be present in the aqueous solution or mixture. If the initial bromide ion source is in solid form, it should be dissolved in distilled water to form a dilute aqueous solution which is then subjected to the above procedure.

The terms "active halogen" and "active bromine" of course refer to all halogen-containing or bromine-containing species, respectively, that are formed in the process and are capable of exhibiting or providing biocidal activity. It is generally accepted in the art that all of the halogen such as bromine in the +1 oxidation state is biocidally active and is thus included in the term "active halogen" or "active bromine", as the case may be. As is well known in the art, chlorine, hypochlorous acid, hypochlorite ion, hydrogen trichloride, trichloride ion, chloride ion, and organo-N-chlorinated compounds, have chlorine in the +1 oxidation state. As is also well known in the art, bromine, bromine chloride, hypobromous acid, hypobromite ion, hydrogen tribromide, tribromide ion, and organo-N-brominated compounds have bromine in the +1 oxidation state. Thus any of these chlorine-containing species and/or bromine-containing species, as well as any other such species to the extent they are present, may constitute the active halogen or active bromine content of the compositions of this invention. For further discussions on this topic one may refer, for example, to U.S. Pat Nos. 4,382,799 and 5,679,239.

Thus, the precise chemical structure(s) of the active halogen in the product solutions formed pursuant to this invention is not critical. Much, if not all, of the active halogen in the product solution will usually be composed of one or more active bromine species (the noun "species" if not enumerated denoting either singular or plural). However, excess hypochlorite if present, and/or some of the chlorine atoms from the hypochlorite may be transitorily present as active chlorine species. Thus to avoid hypercritical nitpicking, reference is made herein to "active halogen", whatever may be the actual entities involved.

It has long been known that the concentration of active halogen in aqueous product solutions of the types produced herein can be readily and accurately determined analytically by means of starch-iodine titration, regardless of what species may constitute the active halogen. Chapter XIV of Willard-Furman, *Elementary Quantitative Analysis*, Third Edition, D. Van Nostrand Company, Inc., New York, Copyright 1933, 1935, 1940 provides a description of starch-iodine titration. While details of standard quantitative analytical procedures for determination of active halogen in such product solutions by starch-iodine titration may vary from case to case, the results are normally sufficiently uniform from one standard procedure to another as not to raise any question of unreliability of the results. Use of the following starch-iodine titration procedure is recommended: A magnetic stirrer and 50 milliliters of glacial acetic acid are placed in an iodine flask. The sample (usually about 0.2–0.5 g) for which the active halogen is to be determined is weighed and added to the flask containing the acetic acid. Water (50 milliliters) and aqueous potassium iodide (15%, wt/wt; 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active halogen is calculated using the weight of the sample and the volume of sodium thiosulfate solution titrated. In this way, the amount of active halogen such as active bromine in an aqueous product solution, regardless of actual chemical form, can be quantitatively determined.

In the conduct of the process technology of this invention, the temperature of the oxidation of the water-soluble bromide ion source such as sodium bromide is preferably kept below about 35° C. and more preferably below about 20° C. Preferred oxidants are alkali or alkaline earth metal hypochlorites such as sodium hypochlorite, potassium hypochlorite, lithium hypochlorite, magnesium hypochlorite, and calcium hypochlorite. The amount of oxidant, such as hypochlorite solution, relative to the bromide source, while not critical, is typically at least a stoichiometric amount, i.e., the amount required to oxidize all of the bromide source present in the reaction solution to active bromine species. An excess over stoichiometric can be used. The aqueous hypochlorite solution itself that is mixed with the bromide source should be relatively concentrated (e.g., in the range of about 10 to about 15 wt % of available chlorine) so that the resultant reaction solution does not contain an excessive amount of water. The water-soluble bromide ion source can be in the form of an aqueous solution or in an undissolved state when the mixing with the hypochlorite solution occurs. Preferably the bromide ion source is used in the form of an aqueous solution which also is a relatively concentrated solution, e.g., in the range of a 40 to 46 wt % solution. The proportions of these reactants used are typically such as to result in the formation of a product solution containing at least about 4 wt %, and preferably at least 6 wt %, of active halogen as determinable by a standard starch-iodine titration procedure.

It is surprising that the ppm quantities of the methanol impurity would or could cause the problems referred to above. Due to the temperature and pH conditions of the reaction, methanol would be expected to be inert and thus not react with the components of the reaction mixture. This however has been discovered not to be the case, and the alcohol is indeed detrimental due to it causing a reduction in the active halogen content of the final product solution. Therefore, pains must be undertaken to ensure that the soluble bromide source is indeed free of alcohol, or contains alcohol at such a low enough level that it is not considered detrimental. We cannot yet put forth a theory as to why the alcohol is detrimental at the temperature and pH conditions of the reaction.

It is very likely, if not a certainty, that the presence of alcohol in alkali metal bromide used in other processes for making concentrated aqueous active-bromine biocidal solutions will cause similar problems of loss of active bromine. As an example, the processes described in U.S. Pat. No. 6,007,726 to Yang et al, the entire disclosure of which is incorporated herein by reference, involve providing a solution of alkali or alkaline earth metal bromide, preferably sodium bromide, and a halogen stabilizer selected from a specified group of stabilizers, adjusting the pH to a pH range of from 4 to 8, followed by the step of adding an oxidizer to the solution.

Thus, pursuant to another embodiment of this invention there is provided an improved process which comprises 1) providing a solution of alkali or alkaline earth metal bromide and a halogen stabilizer, said solution being free of a detrimental quantity of any alcohol;

2) adjusting the pH of solution provided in 1) to a pH range of from 4 to 8; and 3) mixing to solution from 2) an oxidizer, preferably an oxidizing bromine compound, to generate at least one oxidizing bromine compound in the solution.

By conducting this process in the absence of a detrimental quantity of alcohol such as methanol, the problems due to the presence of such ppm quantities of alcohol are eliminated.

Still other processes which can benefit from the practice of this invention are those described in U.S. Pat. No. 6,156,229 to Yang et al, the entire disclosure of which is incorporated herein by reference. In the processes of that patent, an alkali or alkaline earth metal bromide and an alkali or alkaline earth metal bromate are mixed in water to form a solution which is cooled, and a specified halogen stabilizer is added to the solution whereby a more stable oxidizing bromine compound is formed in the solution. Pursuant to a further embodiment of this invention there is provided a process which comprises generating an oxidizing bromine compound of enhanced stability, which process comprises:

A) mixing an alkali or alkaline earth metal bromide and an alkali or alkaline earth metal bromate in water in the absence of a detrimental quantity of any alcohol, to form an aqueous solution;

B) cooling solution formed in A), preferably to less than about 25° C.; and

C) adding a halogen stabilizer to cooled solution from B).

If it is desired to utilize in any previously disclosed process such as any process of U.S. Pat. Nos. 5,683,654; 5,795,487; 5,942,126; 6,007,726; or 6,156,229, the improvement based on the discoveries of this invention comprising conducting the process in the absence of a detrimental quantity of any alcohol, e.g., methanol, it is appropriate to employ the applicable process details, preferred materials, etc., as set forth in the applicable patent disclosure.

The following non-limiting Examples further illustrate the improved technology provided by this invention. In these Examples, the sodium bromide used was prepared in the laboratory without any exposure whatever to any alcohol, so that it was devoid of any alcohol impurity. Examples 1 and 2 were conducted in accordance with this invention whereas Example 3 is a Comparative Example not of this invention. Example 1 represents a preferred embodiment.

EXAMPLE 1

A 500 mL fully-jacketed flask is charged with 177.7 g of 45 wt % of an alcohol-free aqueous sodium bromide solution, and is cooled by a glycol bath to 15° C. Then, following an initial charge of 0.2 g of sulfamic acid, a feed of sodium hypochlorite solution (410 g, 13.46 wt % active chlorine, 4.5 mL/min) is initiated. The reaction solution is maintained at 15–17° C. throughout the addition of the sodium hypochlorite solution. Also, during the sodium hypochlorite feed sulfamic acid is added to the reaction solution at a rate that maintains the pH of the reaction solution between 2.5–4. At the end of the bleach feed of approximately 75 minutes duration, the amount of sulfamic acid remaining out of an overall total of 83.2 grams (i.e., including the initial charge of 0.2 g) is added to the flask. After stirring for 15 minutes, 117.1 g of 50% aqueous caustic is added to complete the reaction. No dilution water is added. The entire process is conducted in the absence of any alcohol.

EXAMPLE 2

The procedure of Example 1 is repeated except that the 45 wt % of alcohol-free aqueous sodium bromide solution is treated with methanol in an amount so as to provide 0.056 wt % of methanol based on the total mass (weight) of all components, and 177.7 g of this alcohol-containing aqueous solution is fed to the flask instead of the alcohol-free aqueous solution.

COMPARATIVE EXAMPLE 3

The procedure of Example 2 is repeated except that the 45 wt % of alcohol-free aqueous sodium bromide solution is treated with methanol in an amount so as to provide 0.228 wt % of methanol based on the total mass (weight) of all components. As in Example 2, 177.7 g of this alcohol-containing aqueous solution is fed to the flask instead of the alcohol-free aqueous solution.

In each of Examples 1–3 the activity of the product solution in terms of wt % active chlorine was determined immediately after the reaction and then for the next few days using the above starch-iodine titration procedure, as shown in the Table. During this period of time after preparation, the solutions were kept in high density polyethylene bottles stored in a closed cabinet to protect the solutions from exposure to UV light.

TABLE

Product Activity (wt % chlorine)

wt % Methanol (based on total reaction mass)

| Day | 0.00 | 0.056 | 0.228 |
|---|---|---|---|
| 0.00 | 6.88 | 6.65 | 6.52 |
| 1 | | 6.54 | 5.42 |
| 2 | 6.88 | 6.50 | 5.34 |
| 3 | 6.84 | | |
| 9 | | 6.57 | 5.41 |
| 10 | 6.88 | | |
| Difference | — | 0.31 | 1.47 |
| Loss in Activity | — | 4.5% | 21.4% |

It can be seen that in the total absence of alcohol there was, within the limits of the starch-iodine analysis procedure used, no loss of active halogen content during the 10-day period. Although there was some loss of active halogen in Example 2, the loss was within acceptable limits. However, in the case of Comparative Example 3 the loss of active halogen content was intolerable and unacceptable. In addition to the changes in active halogen shown in the Table, it was found that losses in free caustic values consistent with loss of product activity was also experienced in Example 2 and Comparative Example 3, whereas the product solution from Example 1 showed no detectable activity loss or free caustic loss during this same period of storage time.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. In a process in which an aqueous solution of a water-soluble alkali metal bromide is oxidized in an aqueous medium to form a microbiocidal solution containing at least 4 wt % of active halogen species as determinable by starch-iodine titration, the improvement wherein the alkali metal bromide used in the process is free of a detrimental amount of alcohol impurity and wherein the process is conducted in the absence of a detrimental amount of alcohol.

2. The improvement according to claim 1 wherein said alkali metal bromide is sodium bromide.

3. The improvement according to claim 1 wherein the amount of alcohol impurity in said aqueous medium is 0.06 wt % or less.

4. The improvement according to claim 1 wherein said microbiocidal solution contains at least 6 wt % of active halogen species as determinable by starch-iodine titration.

5. The improvement according to claim 4 wherein said alkali metal bromide is sodium bromide.

6. The improvement according to claim 4 wherein the amount of alcohol impurity in said aqueous medium is 0.06 wt % or less.

7. The improvement according to claim 6 wherein said alkali metal bromide is sodium bromide.

8. An aqueous microbiocidal solution having a pH of at least about 13 containing, as determinable by starch-iodine titration, at least 4 wt % of stabilized active halogen species formed by oxidation of an alkali metal bromide and incorporation of a stabilizer for the active bromine, said solution being characterized in that for at least the 10-day period immediately following its preparation, said product solution contains either no detectable quantity of an alcohol or no more than about 0.11 wt % of an alcohol.

9. A solution according to claim 8 wherein said alkali metal bromide is sodium bromide.

10. A solution according to claim 8 wherein said solution contains at least 6 wt % of stabilized active halogen species as determinable by starch-iodine titration, wherein said product solution contains either no detectable quantity of an alcohol or no more than about 0.06 wt % of an alcohol, and wherein the stabilizer used is a source of sulfamate anion.

11. A solution according to claim 10 wherein said alkali metal bromide is sodium bromide.

12. A solution according to claim 8 wherein said solution contains a detectable quantity of an alcohol.

13. A solution according to claim 12 wherein said alcohol consists essentially of methanol.

14. A solution according to claim 13 wherein said alkali metal bromide is sodium bromide.

15. A solution according to claim 10 wherein said solution contains a detectable quantity of an alcohol.

16. A solution according to claim 15 wherein said alcohol consists essentially of methanol.

17. A solution according to claim 16 wherein said alkali metal bromide is sodium bromide.

* * * * *